United States Patent [19]
Petit

[11] Patent Number: 6,027,524
[45] Date of Patent: Feb. 22, 2000

[54] IMPLANTABLE ILLUMINATOR FOR PHOTODYNAMIC THERAPY OF THE BREAST AND METHOD

[76] Inventor: Michael G. Petit, 841 Weldon Rd, Santa Barbara, Calif. 93109

[21] Appl. No.: 09/044,553

[22] Filed: Mar. 19, 1998

Related U.S. Application Data

[62] Division of application No. 08/889,020, Jul. 7, 1997, Pat. No. 5,766,222.

[51] Int. Cl.$^7$ ..................................................... A61B 17/36
[52] U.S. Cl. ................................................ 607/91; 606/16
[58] Field of Search ................................ 606/2, 9, 10, 11, 606/12, 13, 14, 15, 16, 17

[56] References Cited

U.S. PATENT DOCUMENTS

| | | | |
|---|---|---|---|
| 4,612,938 | 9/1986 | Dietrich et al. | 606/12 |
| 4,998,930 | 3/1991 | Lundahl | 606/15 |
| 5,125,925 | 6/1992 | Lundahl | 606/15 |
| 5,354,293 | 10/1994 | Beyer et al. | 606/16 |
| 5,527,308 | 6/1996 | Anderson et al. | 606/15 |

*Primary Examiner*—Linda C. M. Dvorak
*Assistant Examiner*—Sonya C. Harris
*Attorney, Agent, or Firm*—Michael G. Petit

[57] ABSTRACT

A device for delivering phototherapeutic light to the nipple and surrounding tissue of a breast. Many mastectomy procedures for patients with breast cancer require removal of the nipple. Thus, for the best aesthetic result, post-operative augmentation or reconstruction of the breast includes the implantation of an artificial nipple. The present device and method permits a more conservative mastectomy to be performed while reducing the risk of recurrence wherein cancerous and pre-cancerous tissue in the nipple and surrounding aureole tissue are treated by illuminating the tissue with phototherapeutic light. The tissue is first perfused with a photosensitizer which accumulates therewithin. An embodiment of the device, which includes a rigid or semi-rigid hemispherical shell for structural stability, is attached to the breast. The device includes a transparent flexible aperture which is designed to fit snugly against the outer surface of the nipple and surrounding tissue. Phototherapeutic light from a light source enters the shell by means of a fiber optic and is conducted to a light diffuser tip disposed within the shell in optical communication with the light output end of the fiber optic. The light emanating from the diffuser tip is reflected from the interior surface of the hemispherical shell to uniformly illuminate the nipple and surrounding photosensitizer-laden tissue. In another embodiment a tissue expander is implanted within the breast following mastectomy. The tissue expander is adapted to receive light from a light source via a fiber optic and deliver diffuse phototherapeutic illumination to the tissue adjacent to and surrounding the tissue expander.

1 Claim, 2 Drawing Sheets

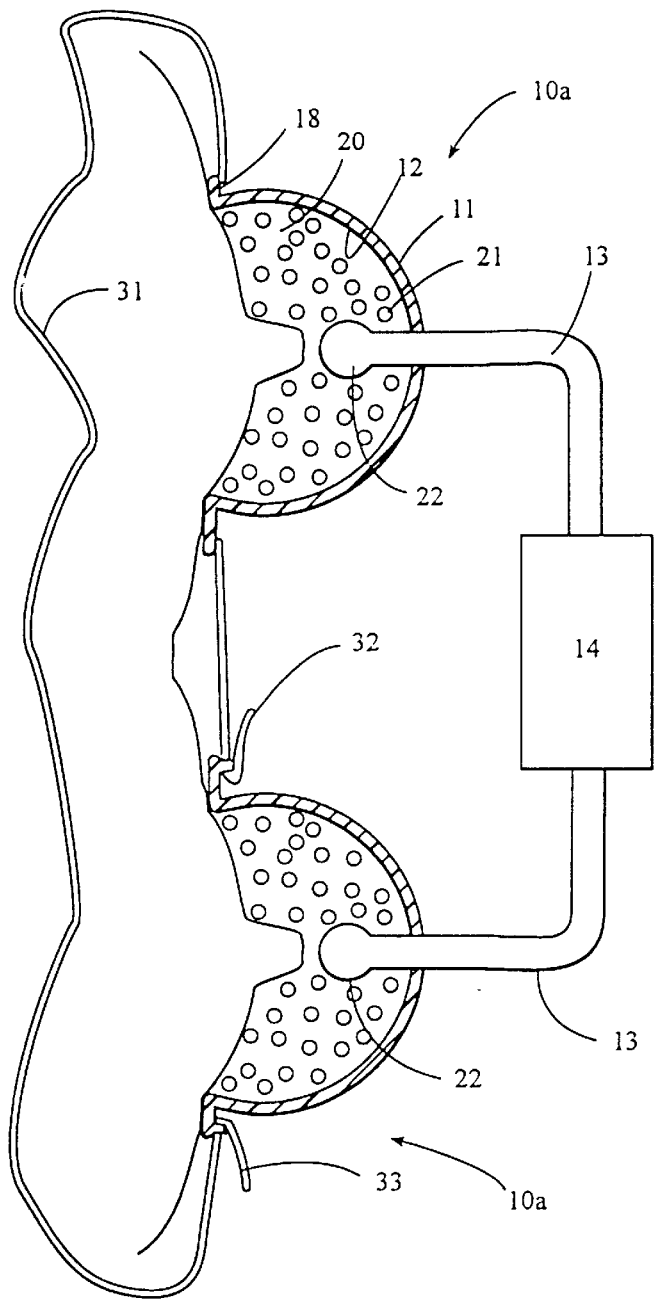
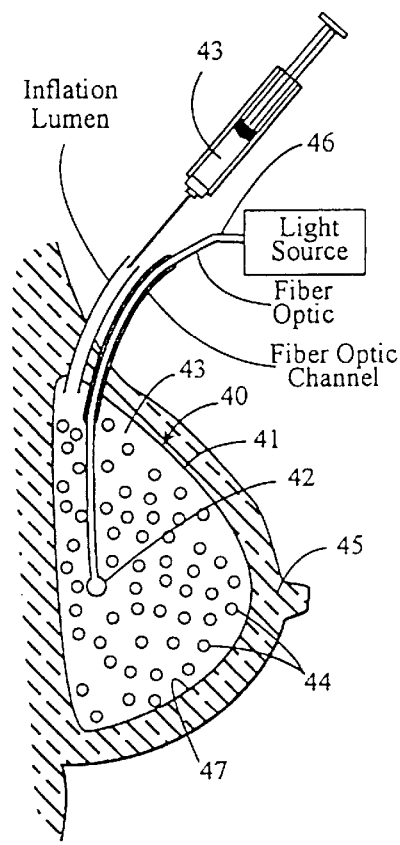
Figure 3
Figure 4

6,027,524

IMPLANTABLE ILLUMINATOR FOR PHOTODYNAMIC THERAPY OF THE BREAST AND METHOD

BACKGROUND OF THE INVENTION

This application is a divisional of Ser. No. 07/889,020 filed Jul. 7, 1997, now U.S. Pat. No. 5,166,222.

1. Field of the Invention

The invention relates to a light delivery device for uniformly illuminating the nipple and surrounding tissue of a breast.

2. Prior Art

Ductile carcinoma in situ (DCIS) is the most common form of breast cancer. The treatment of choice for DCIS depends upon the stage of growth of the tumor. For small tumors, that is, tumors less than 1 or 2 centimeters in diameter, a lumpectomy followed by radiation treatment to the affected breast is conventional. If there is more extensive involvement and/or there is an invasive component present it may be preferable to perform a mastectomy. A conventional mastectomy, when DCIS is present includes the removal of the nipple. The reason for this is that much of the pre-cancerous cell are contained within the milk ducts of the breast. Since the nipple area is rich in milk ducts, it is prudent to remove the entire nipple.

The use of photodynamic therapy for treating breast cancer has been restricted due to the limited ability of light to penetrate tissue. Whole breast illumination is not practical at present because a dosage of phototherapeutic light having a wavelength suitable for administering photodynamic therapy only penetrates to an extent to about 1 centimeter in depth. Thus, the conventional mastectomy is the most commonly employed procedure for treating advanced stages of DCIS. In addition, even with nipple excision, some tissue remains behind following a mastectomy, adhering to the overlying skin, which tissue may include cancerous or precancerous cells.

If it were possible to provide a more conservative approach by saving the nipple, this would facilitate reconstruction of the breast and provide the patient with a superior appearance following surgery. Thus, there is a need for a method for treating patients presenting with DCIS by employing photodynamic therapy to the nipple and surrounding tissue to destroy cancer cells which will enable a mastectomy to be performed without the necessity of removing the nipple while minimizing the risk of recurrence.

SUMMARY OF THE INVENTION

It is an object of this invention to provide a device for delivering illumination uniformly to the nipple and the surrounding tissue of a patient with DCIS in a therapeutically effective dosage of light.

It is another object of this invention to provide a method for destroying cancer and pre-cancerous cells in the nipple and surrounding tissue of the breast.

It is a further object of this invention to provide a tissue expander for temporary implantation within the breast which can be used for administering photodynamic therapy to the surrounding tissue.

The features of the invention believed to be novel are set forth with particularity in the appended claims. However, the invention itself both as to organization and method of operation together with further objects and advantages thereof may best be understood by reference to the following description taken in conjunction the accompanying drawings in which:

BRIEF DESCRIPTION OF THE DRAWINGS

FIG. 3 is a third preferred embodiment of the device of the present invention wherein a pair of identical devices is used to uniformly illuminate the nipple and surrounding tissue of both breasts.

FIG. 4 is an elevational cross-sectional view of an inflatable tissue expander device adapted to receive phototherapeutic light from a light source and deliver the light diffusely to the surrounding tissue.

DESCRIPTION OF THE PREFERRED EMBODIMENTS

Figure 1:
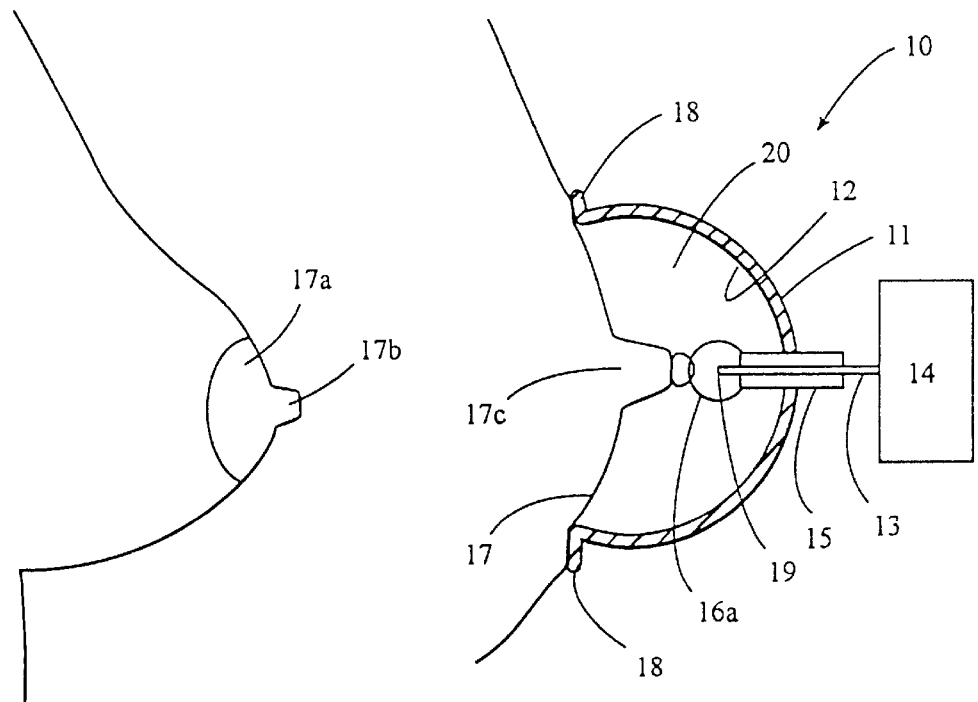
FIG. 1 is a cross sectional schematic view of a first preferred embodiment of a light delivery device in accordance with the present invention adapted for illuminating the nipple and surrounding tissue of a human breast.

Turning now to FIG. 1, a first preferred embodiment of the device suitable for illuminating the nipple and surrounding tissue of a breast to a depth of about 1 cm below the skin surface is shown at 10. The device 10 comprises an outer, substantially hemispherical shell 11 of a rigid or semi-rigid material having an inner reflective surface 12 coating the interior surface thereof A fiber optic 13 conducts light from a light source 14 through an optical connector feedthrough 15 to illuminate a convex reflector 16 in optical communication therewith. A transparent silicone membrane 17 having an indentation 17c, pre-formed to conform to the shape of a portion of a human breast comprising the nipple 17b, encloses the open end of the hemispherical shell 11 and forms the light output aperture of the device. The convex reflector 16 is attached to the feed through 15 by means of a rigid transparent bulb 15a and disposed adjacent to the flexible transparent membrane 17 at the apex portion of the device where the tip of the nipple 17b will be placed. The spherical bulb 16a, in rigid attachment to the convex reflector 16 and the fiber optic feedthrough 15, keeps the light output end 19 of the fiber optic 13 in optical alignment with the optic axis A (FIG. 2) of the hemispherical reflector 16 and fiber optic 13. The interior volume 20 of the device 10, which interior volume 20 is enclosed by the shell 11 and the transparent membrane 17, contains an optically transparent fluid such as water or a low viscosity deformable gel such as silicone gel or hydrogel. Phototherapeutic light from a light source 14 is conducted via the fiber optic 13 to the light output end 19 where it emerges to impinge upon the convex reflector 16. The light is reflected from the surface of the convex reflector 16 to impinge upon the reflective inner surface 12 of the shell 11 where the light is re-reflected and exits the interior volume 20 through the aperture provided by the transparent membrane 17 and enters the skin.

Figure 2:
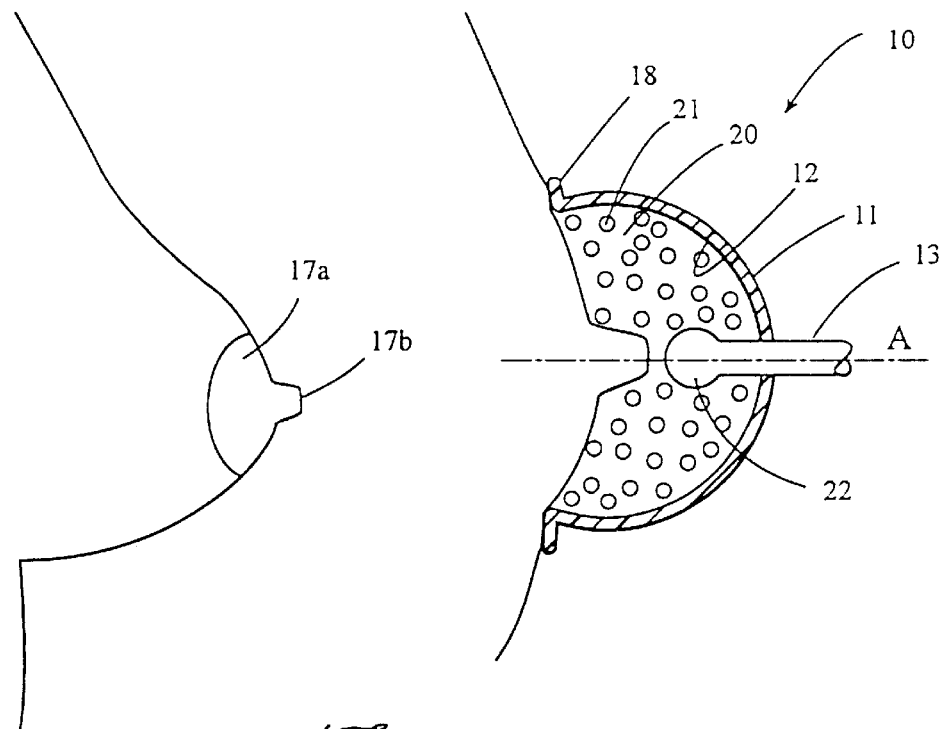
FIG. 2 is a schematic drawing of a second preferred embodiment of a light delivery device suitable for illuminating the nipple and surrounding tissue of the breast wherein a light scattering medium is included within the interior of the device to provide more diffuse illumination at the output aperture.

FIG. 2 shows a second preferred embodiment of a device in accordance with the present invention which is similar to the embodiment of FIG. 1. The fiber optic 13 has a light output terminus 22 comprising a spherical diffuser tip. The interior cavity within the shell is filled with a transparent medium having optically scattering centers 21 dispersed therethroughout light emanating from the diffuser tip 22 spherically illuminates the interior portion of the shell and reflects off the reflective inner surface 12 and is directed toward the nipple and the surrounding tissue. The apex of the nipple 17b is placed within the conforming curvature of the recess 17c molded into transparent membrane 17 in snug engagement therewith. Flexible lugs 18 projecting laterally from the shell 11 provide means for attaching the devices to each other (if more than one is used as shown in FIG. 3) and/or to the body of a patient.

A third preferred embodiment of the device of the present invention is shown at 10a in FIG. 3. In FIG. 3, two identical nipple illuminator devices 10a are connected by means of an adjustable connecting strap 32. The outer lug 18 on one end of the device engages the adjustable strap 31 attached to the outer lug 18 on the other light delivery device to enable the user to fasten the device around the chest. Depending on the condition of the breasts (i.e. the presence of bilateral cancer) one or both devices may be illuminated. A light source may be employed which is in optical communication with both devices and which can be attached to the body for wearing.

The device may be used to illuminate the breast in the following manner. A suitable photodynamically active photosensitizing agent such as, for example, tinethyletiopurpurin or a hematoporphyrin derivative is injected into the patient and allowed to perfuse the breast where it will accumulate within the cancerous and pre-cancerous tissue (target tissues) of the breast. After a suitable period of time has elapsed to permit accumulation of the photosensitizer within the target tissue, the device is attached to the breast such that the nipple 17b and the surrounding aureole tissue 17a are pressed against the transparent membrane 17 of the device with the nipple centered within the recess 17c. The device 10 is affixed to the chest wall by means of flexible lugs 18 which may be taped to the chest or connected to one another by means of a strap which extends around the chest of the patient. A light source 14 is activated to provide phototherapeutic light which is conducted to diffuser tip 22 by means of fiber optic 13 to illuminate the interior of the device(s). A pickup fiber (not shown) may be used to monitor the dosage of phototherapeutic light actually delivered to the tissue. After a sufficient dosage of light has been administered to effect therapy, the light source is disconnected and the device removed from the breast. The above procedure may be used either before or after the mastectomy. The foregoing method provides means for conserving the nipple and surround tissue during a mastectomy while minimizing the patient's risk of recurrence.

PDT may also be employed post-operatively to treat any remaining tissues containing DCIS which are attached to the skin following partial or total removal of breast tissue. A tissue expander device may be placed beneath the skin and disposed within the pocket remaining following mastectomy. Tissue expander devices are well known in the art. Examples of such devices are shown in U.S. Pat. Nos. 4,841,948 to Bauer et. al. and 4,671,255 to Dubrul et. al. The inflatable portion of the device is implanted beneath the skin within the dissected cavity where tissue has been removed, and slowly inflated. The overlying skin stretches to accommodate the increasing volume of the tissue expander. Inflation fluid is introduced by transdermal injection into a fill port. The fill port is implant to underlie an accessible portion of the patient's skin. The fill port may be integral with the tissue expander as shown in U.S. Pat. No. 4,671,255 or connected to the inflatable shell by a fill tube as shown in 4,841,948. In any event, the fill port is self-sealing to the track of a needle or cannula inserted therein. Other self-sealing fill valves suitable for use with a blunt cannula are described in U.S. Pat. Nos. 4,178,643, 5,084,061 and 5,127,627.

An inflatable tissue expander device suitable for implantation beneath the skin and adapted to deliver phototherapeutic light to the surrounding tissue is shown in elevational cross-section in FIG. 4. The transparent shell 41 of the tissue expander 40 is adapted to transmit a portion of the phototherapeutic light incident thereon emanating from a light diffuser element 42 disposed within the interior of the shell. A portion of the light is reflected inwardly to be re-reflected outward. The shell 41 is inflated with an inflation fluid 43 containing light scatterers 44 dispersed therein such as Teflon spheres or silica until the desired volume is achieved. A photosensitizer suitable for performing photodynamic therapy is then injected intravenously into the patient and permitted to accumulate within any residual cancerous tissue 45 remaining following surgical mastectomy. Light is conducted to the diffuser element 42 disposed within the interior of the tissue expander by a fiber optic 46. The light emitted by the diffuser element 42 is scattered by the inflation medium 43 prior to impinging on the shell thereby further diffusing the light. A portion of the scattered light incident upon the inner surface 47 of the shell 41 is transmitted therethrough to diffusely illuminate the tissue surrounding the tissue expander including the muscles overlying the chest wall. The correct dosage of light required to effect photodynamic therapy of diseased tissue is then administered.

A fiber optic, such as described in U.S. Pat. Nos. 5,196,005 and 5,237,638, may conveniently be inserted through a cannula guide into the injection port or valve and into the interior of a tissue expander to conduct light to a diffuser tip disposed in the interior thereof. A partially reflective coating such as gold or silver on the inner surface of the tissue expander promotes multiple reflections of treatment light within the interior of the expander thereby facilitating more uniform delivery of light to the surrounding tissue.

While particular embodiments of the present invention have been illustrated and described, it would be obvious to those skilled in the art that various other changes and modifications can be made without departing from the spirit and scope of the invention. For example, the hemispherical shell 11 may include a soft, flexible peripheral flange around the perimeter thereof which conforms to surface contours of the skin. It is therefore intended to cover in the appended claims all such changes and modifications that are within the scope of this invention.

What I claim is:

1. A method for treating ductile carcinoma in situ by administering phototherapy to the nipple and surrounding tissue of a breast comprising the steps of:

(a) performing a surgical mastectomy or lumpectomy to remove cancerous or pre-cancerous tissue without removing the nipple or surrounding tissue; and (b) administering photodynamic therapy to the nipple and surrounding tissue.

\* \* \* \* \*